(12) United States Patent
Reddy et al.

(10) Patent No.: US 9,993,573 B1
(45) Date of Patent: Jun. 12, 2018

(54) ODOR NEUTRALIZER

(71) Applicant: APPTEC, Inc., Cranbury, NJ (US)

(72) Inventors: Vilambi Nrk Reddy, Cranbury, NJ (US); Anil Torgalkar, Cranbury, NJ (US)

(73) Assignee: APPTEC, Inc., Cranbury, NJ (US)

( * ) Notice: Subject to any disclaimer, the term of this patent is extended or adjusted under 35 U.S.C. 154(b) by 103 days.

(21) Appl. No.: 15/400,996

(22) Filed: Jan. 7, 2017

(51) Int. Cl.
 *A61L 9/013* (2006.01)
(52) U.S. Cl.
 CPC .................................. *A61L 9/013* (2013.01)
(58) Field of Classification Search
 None
 See application file for complete search history.

(56) References Cited

U.S. PATENT DOCUMENTS

2011/0052737 A1\* 3/2011 Florence .................. A61K 8/97
 424/742

\* cited by examiner

*Primary Examiner* — Hasan S Ahmed
*Assistant Examiner* — Frank Choi
(74) *Attorney, Agent, or Firm* — Stanley H. Kremen

(57) ABSTRACT

A combination of herbal extracts in aqueous solution that when sprayed into a confined area as a fine mist, chemically neutralizes a wide range of odors including those that are acidic, alkaline, and neutral in nature. While this chemical solution may contain fragrances, odor elimination occurs chemically rather than by masking.

15 Claims, No Drawings

ODOR NEUTRALIZER

BACKGROUND OF INVENTION

Consumer desires to eliminate noxious odors has fueled a modern industry beginning in the twentieth century. Some bad odors can be eliminated merely by lighting a match or otherwise using fire. In the 1960's, Renuzit® marketed spray cans that filled the surrounding air with fragrances, such as baby powder, to mask odors. These were and are still marketed by that company as air fresheners. Today, Renuzit® sells "cones" containing fragrance gels and "pearls" that both absorb odors and emit pleasing fragrances. Air fresheners are marketed by Glade®, which also markets odor eliminating candles. Rubbermaid® sells plug-in cartridges that continuously fill a room with a desired fragrance (e.g., citrus scent). Odorklenz® sells products that neutralize some odors such as those from urine. Duluth Trading Co. sells an "odor eliminator" that runs on four C-batteries and uses electrically charged "activated oxygen" in footwear and gloves. This device claims to eliminate odors arising from sweat, mold, mildew, germs, toxins, and pollutants. Hamilton Beach® sells an electronic True Air® Room Odor Eliminator that uses a fan to force room air through three carbon filters, which neutralize the odors, and optionally add fragrances to the air. Biocide Systems™ markets a product that uses chlorine dioxide (ClO2) to neutralize odors. This product, when exposed to the air in a room, neutralizes cigarette smoke odors, skunk odors, cooking odors, and cat urine odors in carpets. The Gonzo® Odor Eliminator uses volcanic minerals to neutralize odors. OdorFree sells ozone generators that neutralize odors. However, free ozone in a room can be toxic to humans. Rocco & Roxie™ Supply Company produces an enzyme spray product to eliminate stains and odors. In 1996, Proctor & Gamble began marketing a product called Febreze®. This product utilizes cyclodextrin (hydroxyl-propyl-beta-cyclodextrin) as its active ingredient. This chemical does not neutralize odors, but rather inhibits the ability for humans to detect the odors. Some sources state that Febreze® also contains zinc chloride, which neutralizes sulfur odors, such as from onions and rotten eggs. However, zinc chloride is not listed as one of the ingredients of Febreze®. All of these products are just examples of products in this crowded industry.

Noxious odors can be divided into three categories, i.e., acidic odors, basic (or alkaline) odors, and neutral odors. Examples of acidic odors include hydrogen sulfide (H2S) [e.g., hard boiled or rotten eggs] and skunk. Examples of alkaline odors include ammonia, urine, and fish smells. Examples of neutral odors include body odors and putrid odors.

It would be desirable to have a non-toxic, water based, natural, herbal extract odor neutralizing substance that can be sprayed into a room or other confined area which would neutralize acidic, alkaline, and neutral odors. Although, such a product could include fragrances, the purpose of such a product would be to neutralize the odor rather than to mask the odor.

SUMMARY OF THE INVENTION

The Present Invention is a combination of herbal extracts in aqueous solution that when sprayed into a confined area as a fine mist, chemically neutralizes a wide range of odors including those that are acidic, alkaline, and neutral in nature. While this chemical solution may contain fragrances, odor elimination occurs chemically rather than by masking.

DETAILED DESCRIPTION OF THE INVENTION

The water based solution of the Present Invention comprises extract of the following plants:

T. indica
   Tamarindus indica
   Tamarind
R. sativus
   Raphanus sativus
   Radish
A. strigosa
   Avena Strigosa
   Lopsided Oat a.k.a. Bristol Oat
C. aurantiifolia
   Citrus x aurantiifolia
   Key Lime
A. fificuloides
   Azolla fificuloides
   Water Fern
L. albus
   Lupinus albus
   White Lupin a.k.a. Field Lupin
O. sanctum
   Ocimum tenuiflorum
   Holy Basil a.k.a. tulasi or tulsi
C. camphora
   Cinnamomum camphora
   Camphor The ingredients are all water soluble. The recommended dose is 2-5% diluted in water. The aqueous solution could also include surfactants, fragrances, buffers, and preservatives. In addition, cyclodextrin may be included as an ingredient. The pH range can be anywhere between 4.1-6.7. It has been experimentally proven that the aqueous solution described above eliminates the following odors and has been utilized in the following applications:

| ODOR | APPLICATION |
| --- | --- |
| Fecal & Urine | Chemical & Plastic Manufacturing |
| Vomit & Soiled | Diaper Pesticides & Herbicides |
| Pet & Kitty Litter | Metal Cutting & Wire Drawing |
| Dead animals & Rotting flesh | Landfills |
| Fish Smell | Pharmaceutical |
| Cooking | Food Processing Plant |
| Garbage | Electric Furnace |
| Skunk Smell | Steel manufacturing |
| Cigarette Smoke | Foundry operations |
| Musty mildew | Heat Press |
| Kitchen & Bathroom | Hospitals & Nursing Homes |
| Basement & Attic | Waste Water Treatment |
| Locker rooms | Composting |
| Automobile & Boat cabins | Refineries |
| Foot/Shoe | Rubber Processing |
| Grease Trap | Tire Manufacturing |
| Sewage | Paper Mills |

As a water based solution, it contains no alcohol. When the solution is sprayed into a confined volume as a fine mist, the ingredients from the solution chemically combine with the organic and inorganic odor producing materials, and converts them into stable and non-toxic substances. The mist permanently destroys malodors on contact. The solution is biodegradable and environmentally friendly. It does not harm human skin. It is safe to use around pets and people.

The individual ingredients listed above may be microencapsulated to eliminate interaction, but this is not necessary.

THE INGREDIENTS

*T. indica*
*Tamarindus indica*
Tamarind

The tamarind tree produces edible, pod-like fruit which is used extensively in cuisines around the world. Because of the tamarind's many uses, cultivation has spread around the world in tropical and subtropical zones. The evergreen leaves are alternately arranged and pinnately compound. The leaflets are bright green, elliptical ovular, pinnately veined, and less than 5 cm (2.0 in) in length. The branches droop from a single, central trunk as the tree matures and is often pruned in agriculture to optimize tree density and ease of fruit harvest. At night, the leaflets close up. The tamarind does flower, though inconspicuously, with red and yellow elongated flowers.

*R. sativus*
*Raphanus sativus*
Radish

The radish (*Raphanus sativus*) is an edible root vegetable of the Brassicaceae family that was domesticated in Europe in pre-Roman times. Radishes are grown and consumed throughout the world, being mostly eaten raw as a crunchy salad vegetable. They have numerous varieties, varying in size, flavor, color, and length of time they take to mature. Radishes owe their sharp flavor to the various chemical compounds produced by the plants, including glucosinolate, myrosinase, and isothiocyanate.

*A. strigosa*
*Avena Strigosa*
Lopsided Oat a.k.a. Bristle Oat

*Avena strigosa* (lopsided oat or bristle oat) is a species of grass native to Europe, and its seeds are edible. This plant is often cultivated as animal feed in the south Brazil, and it is sometimes reported as a weed.

*C. aurantiifolia*
*Citrus x aurantiifolia*
Key Lime

*C. aurantiifolia* is a shrubby tree, to 5 m (16 ft), with many thorns. Dwarf varieties exist that can be grown indoors during winter months and in colder climates. Its trunk, which rarely grows straight, has many branches, and they often originate quite far down on the trunk. The leaves are ovate, 2.5-9 cm (1-3½ in) long, resembling orange leaves (the scientific name *aurantiifolia* refers to this resemblance to the leaves of the orange, *Citrus aurantium*). The flowers are 2.5 cm (1 in) in diameter, are yellowish white with a light purple tinge on the margins. Flowers and fruit appear throughout the year, but are most abundant from May to September in the Northern Hemisphere. The key lime (*Citrus x aurantiifolia*) is a citrus hybrid (*C. micrantha* x *C. medica*) with a globose (spherical shaped) fruit, 2.5-5 cm in diameter (1-2 in), that is yellow when ripe but usually picked green commercially.

*A. filiculoides*
*Azolla filiculoides*
Water Fern

*Azolla filiculoides* (Water Fern) is a species of *Azolla*, native to warm temperate and tropical regions of the Americas as well as most of the old world including Asia and Australia. It is a floating aquatic fern, with very fast growth, capable of spreading over lake surfaces to give complete coverage of the water in only a few months. Each individual plant is 1-2 cm across, green tinged pink, orange or red at the edges, branching freely, and breaking into smaller sections as it grows. It is not tolerant of cold temperatures, and in temperate regions it largely dies back in winter, surviving by means of submerged buds. Like other species of *Azolla*, it can fix nitrogen from the air.

*L. albus*
*Lupinus albus*
White Lupin a.k.a. Field Lupin

White lupin is distinct within the vast and polymorphous genus *Lupinus* L. for small variation of morphological characters. However, it has wide intraspecific variability in physiological plant properties: duration of vernalization time and growth rate, photoperiodic sensitivity, shape tolerance, drought resistance, cold- and winter-hardiness. There are winter and spring forms of white lupin. The white lupin is annual, more or less pubescent plant, 30 to 120 cm high, has a wide distribution in the Mediterranean region.

*O. sanctum*
*Ocimum tenuiflorum*
Holy Basil a.k.a. Tulasi or Tulsi

*Ocimum tenuiflorum*, also known as *Ocimum sanctum*, holy basil, or tulasi or tulsi (also sometimes spelled thulasi), is an aromatic plant in the family Lamiaceae which is native to the Indian subcontinent and widespread as a cultivated plant throughout the Southeast Asian tropics. It is an erect, many 22 branched subshrub, 30-60 cm (12-24 in) tall with hairy stems and simple phyllotaxic green or purple leaves that are strongly scented.

*C. camphora*
*Cinnamomum camphora*
Camphor

*Cinnamomum camphora* (commonly known as camphor tree, camphorwood or camphor laurel) is a large evergreen tree that grows up to 20-30 m (66-98 ft) tall.[1] The leaves have a glossy, waxy appearance and smell of camphor when crushed. In spring, it produces bright green foliage with masses of small white flowers. It produces clusters of black, berry-like fruit around 1 cm (0.39 in) in diameter. Its pale bark is very rough and fissured vertically.

We claim:

1. An airborne aqueous formulation comprising water having the following ingredients dissolved therein:
    a) an aqueous extract of *Tamarindus indica,*
    b) an aqueous extract of *Azolla filiculoides,*
    c) an aqueous extract of *Lupinus albus*, and
    d) an effective amount of at least one preservative,
    which when said formulation is introduced into the air in a confined volume, said formulation neutralizes noxious acidic odors, alkaline odors, and neutral odors.

2. The airborne aqueous formulation of claim 1 further comprising an aqueous extract of *Raphanus sativus* dissolved therein.

3. The airborne aqueous formulation of claim 1 further comprising an aqueous extract of *Avena strigosa* dissolved therein.

4. The airborne aqueous formulation of claim 1 further comprising an aqueous extract of *Citrus aurantifolia* dissolved therein.

5. The airborne aqueous formulation of claim 1 further comprising an aqueous extract of *Occimum sanctum* dissolved therein.

6. The airborne aqueous formulation of claim 1 further comprising an aqueous extract of *Cinnamomum camphora* dissolved therein.

7. The airborne aqueous formulation of claim 1 further comprising cyclodextrin.

8. The airborne aqueous formulation of claim 1 further comprising one or more surfactants.

9. The airborne aqueous formulation of claim 1 further comprising fragrances.

10. The airborne aqueous formulation of claim 1 wherein said formulation is an aerosol spray, a vapor, a mist, a fog, or a gas.

11. The airborne aqueous formulation of claim 1 wherein said formulation takes the form of droplets.

12. The airborne aqueous formulation of claim 1 wherein the concentration of the ingredients dissolved in water is in the range of 2-percent to 5-percent by weight.

13. The airborne aqueous formulation of claim 1 wherein the pH of said formulation is in the range of 4.1 to 6.7.

14. The airborne aqueous formulation of claim 1 wherein said formulation does not contain alcohol.

15. The airborne aqueous formulation of claim 1 wherein the ingredients are microencapsulated to eliminate interaction between them.

* * * * *